United States Patent [19]

Parra

[11] Patent Number: 5,031,637
[45] Date of Patent: Jul. 16, 1991

[54] NON-INVASIVE DIAGNOSTIC METHOD AND APPARATUS

[76] Inventor: Jorge M. Parra, 7332 Grand Blvd., New Port Richey, Fla. 34652

[21] Appl. No.: 569,121

[22] Filed: Aug. 17, 1990

[51] Int. Cl.$^5$ .............................................. A61B 7/00
[52] U.S. Cl. ..................................... 128/773; 128/670
[58] Field of Search ................ 128/713, 714, 715, 676, 128/668, 897, 898, 773; 600/21, 26; 340/753, 754, 755, 756

[56] References Cited

U.S. PATENT DOCUMENTS

| | | |
|---|---|---|
| 1,282,908 | 10/1918 | Miller . |
| 3,181,528 | 5/1965 | Brackin . |
| 3,872,443 | 3/1975 | Ott . |
| 4,008,711 | 2/1977 | Olinger et al. . |
| 4,216,766 | 8/1980 | Duykers et al. . |
| 4,226,248 | 10/1980 | Manoli . |
| 4,232,685 | 11/1980 | Nagashima et al. . |
| 4,246,784 | 1/1981 | Bowen . |
| 4,437,473 | 3/1984 | Mollan . |
| 4,571,750 | 2/1986 | Barry . |
| 4,586,514 | 5/1986 | Schlager et al. . |
| 4,672,977 | 6/1987 | Kroll . |
| 4,705,048 | 11/1987 | Pfohl . |
| 4,748,987 | 6/1988 | Barry . |
| 4,805,636 | 2/1989 | Barry et al. . |
| 4,823,807 | 4/1989 | Russell et al. . |
| 4,836,215 | 6/1989 | Lee . |
| 4,836,218 | 6/1989 | Gay et al. . |
| 4,928,705 | 5/1990 | Sekhar et al. . |
| 4,947,859 | 8/1990 | Brewer et al. . |

Primary Examiner—Kyle L. Howell
Assistant Examiner—Robert L. Nasser, Jr.
Attorney, Agent, or Firm—Jim Zegeer

[57] ABSTRACT

Noises made by the flow of blood in the human cardiovascular system and skeletal noises made in the joints of a skeletal animal provide a wide variety of sounds which, when the human body is partially or completely immersed in a body of acoustically transmissive liquid, are directly coupled to the acoustically transmitted liquid and thus launched into the acoustically transmitted liquid. Each joint and/or portion of the cardiovascular system has a unique acoustic signature. Joints, for example, which are injured or diseased have unique acoustic signatures e.g., sounds they make, which are launched into the water and thus each individual's skeletal system make or produce a unique pattern of noise or sounds which are normally inaudible, but when immersed in a body of water can be detected by hydrophones or underwater microphones. The invention has use in locating missing or lost divers, surveillance of bodies of water for serepititous entry thereto, medical diagnosis (both of skeletal and cardiovascular ailments) as well as providing a baseline for future diagnosis.

7 Claims, 2 Drawing Sheets

NON-INVASIVE DIAGNOSTIC METHOD AND APPARATUS

BACKGROUND AND BRIEF DESCRIPTION OF THE INVENTION

Stethoscopes and like apparatus have been used for many years to listen to sounds made by the human body and to make diagnostic analysis of various conditions in the human body. The sounds produced are typically in the sonic range and while stethoscopes are, obviously, widely used by the medical profession, the types of analysis and uses for such apparatus is relatively limited primarily to the chest cavity area (e.g., breathing and gas flow in the lungs, etc.) and for blood pressure readings in the cardiovascular system.

The present invention is directed to a non-invasive diagnostic apparatus and method wherein the human body or a portion thereof is placed in a body of an acoustically transmissive fluid, such body of acoustically transmitting fluid being contained in a container preferably having sidewalls formed of or coated with acoustically absorbent material. One or more hydrophones are located in the body of fluid to detect or "listen" to sounds, such as cardiovascular sounds, gas flow and skeletal sounds made by body movements. These sounds are passed through a preamplifier, a bandpass filter and discriminator, the function of which may be performed by microprocessors to a recorder and/or display device. The recorder can record body sounds much in the fashion of an strip chart recorder used for EKG and/or EEG. Typical pool water with chlorine, or salt water, or oils, such as vegetable oils can be used for the acoustically transmissive medium. In addition to audible sounds, the method and apparatus are particularly useful for listening to infrasonic or subsonic sounds. A feature of the invention is that the subject is placed or immersed in the body of acoustically transmissive liquid in a container having acoustically absorbing walls so that there are no unwanted reflections of sounds launched in the water from the human body reflecting off of the walls. One or more hydrophones located in the body of water are used to detect the sonic energy launched by the human body. The human in the body of acoustic liquid is instructed to go through a particular sequence of movement, for example, the arms, (flexion, extension, abduction, abduction), or the back, or legs (inversion eversion), etc. and record is made the sounds emitted during each of the movements of the specific body parts or the specific movement made by a given patient. For example, an athlete may be asked to bend his or her knee (flexion, extension), elbow (flexion, extension) and the like and a record is made of the sounds generated and launched into the acoustically transmissive liquid. Similar recordings are made for a large number of individuals to provide a norm of the movements of a particular body part in a particular direction and/or at a particular rate of speed. These records then form a database which may be stored in the computer database and used to detect departures from the normal sounds made and thereby provide the physician with a greater body of knowledge to enable successful treatment for the patient.

The above and other objects, advantages and features of the invention will become more apparent when considered with the following specification and accompanying drawings wherein:

FIG. 1 is a perspective isometric view of a apparatus incorporating the invention, FIG. 2 is a diagrammatic illustration of a few movements of the body at the joints (from Wedding et al. "Medical Terminology", copyright 1988), FIG. 3 is a block diagram thereof, FIG. 4 is a detailed block diagram,

DETAILED DESCRIPTION OF THE INVENTION

The non-invasive diagnostic apparatus and method of this invention is performed using a vessel or container 10 which is of sufficient size to at least hold a portion of a human body therein such that the portion can be voluntarily articulated by the human without engaging or contacting the sidewalls. In the illustrated embodiment, the vessel 10 is a large tank in which a human H is immersed up to the neck line. In a preferred embodiment, the sidewalls S1, S2, S3 and S4 and bottom are preferably formed of or coated with an acoustic absorber AB so that there are substantially no reflections of acoustic energy from the sidewalls and that any acoustic energy launched by the human H body, or body parts, are received directly by one or more hydrophones T1, T2 . . . TN, which are oriented to face the human's body. (While in this embodiment, the specimen or patient is a human, it will be appreciated that the same techniques may be used in connection with race horses, dogs, cats and other animals, but, in this preferred embodiment, the invention is particularly applicable to diagnostic purposes for use with humans).

Figure 2:
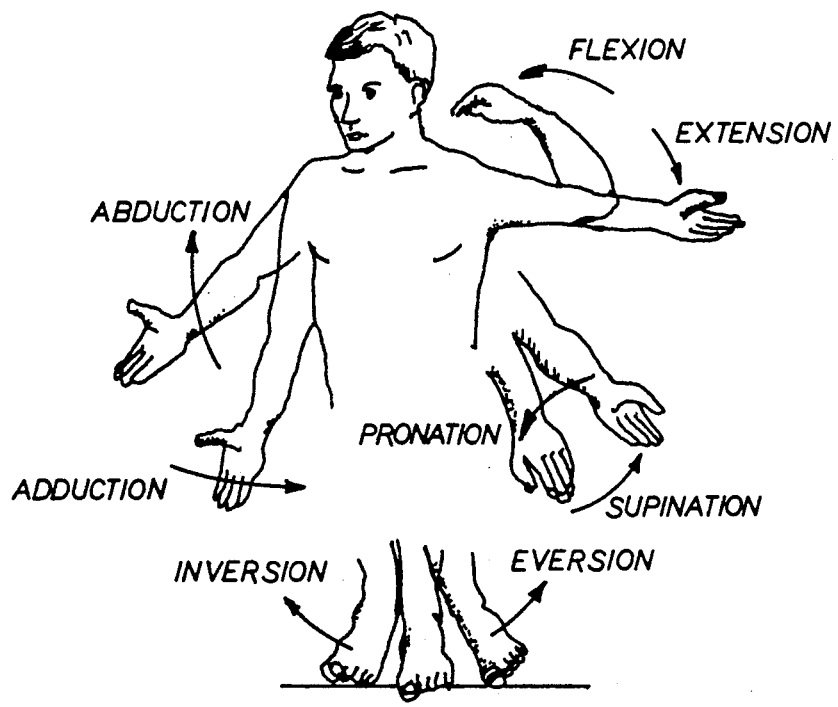

Various movements made by the body at the joints are illustrated in FIG. 2 and these generate sounds. According to the invention, sounds emitted from the human body caused by movements of the skeletal portion (skeletal sounds) and/or blood flow (cardiovascular sounds) and/or air flow are detectable using the invention.

Noises made by the flow of blood in the human cardiovascular system and skeletal noises in the joints of a human skeleton provide a wide variety of sounds (mostly infrasonic) which, when the human body is partially or completely immersed in a body of an acoustically transmissive liquid medium ATL such as water, vegetable oil, etc., are directly coupled to the liquid medium and thus launched into the liquid medium. Each joint, for example, has a unique acoustic signature. Joints which are injured or diseased can have their own unique acoustic signatures or sounds they make which are launched into the liquid medium. Thus, each individual skeletal system make or produces a unique pattern of sonic energy or noise which are normally infrasonic or but, when immersed in a body of acoustically transmissive liquid such as water, vegetable oil and the like, can be detected by hydrophones or underwater microphones T1, T2 . . . TN.

The invention also has use in locating missing or lost divers, surveillance of bodies of water for surreptitious entry to the body of water by humans, and, as discussed extensively above, non-invasive medical diagnosis, both of skeletal, cardiovascular ailments, etc., as well as providing a baseline for future diagnosis.

Figure 1:
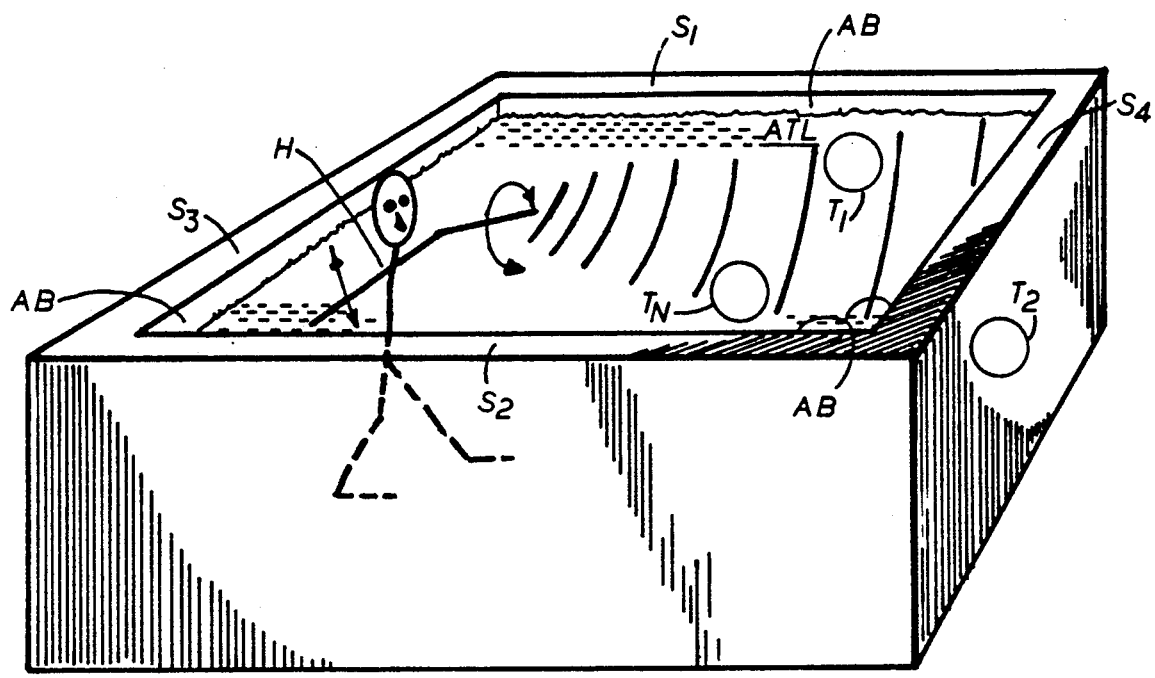

In FIG. 1, the hydrophone or transducers T1, T2 . . . TN may comprise of one or a plurality of different microphones, and are each referred to herein as acoustic transducers and they convert acoustic energy transmitted in the body of acoustically transmissive liquid ATL.

Figure 3:
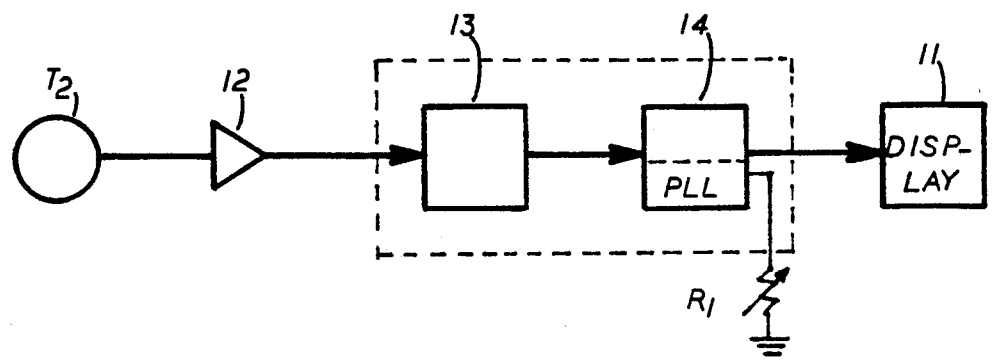

Acoustic transducers T may be positioned in the body of acoustically transmissive liquid ATL or a wall of vessel 10 and converts all sonic energy to electrical signals. As shown in the block diagram of FIG. 3, the electrical signals produced by transducer T2 are amplified by preamplifier 12 and supplied to a bandpass filter 13, the output of which is supplied to a discriminator 14 and then to a display or recorder 11. The bandpass filter removes unwanted background noise and interference and passes the desired cardiovascular and/or skeletal sounds. The configuration of the filter is in a cascaded high-pass/low-pass configuration to maximize attenuation outside the desired frequency. While there are some sounds that are in the audible range, typical sounds made by the movement of the human skeletal system are in the subsonic or infrasonic range and thus in the preferred embodiment, the bandpass filter is designed to restrict frequencies to this. Moreover, the solid state discriminators include a phase lock loop PLL which is adjustable or programmed by adjustable resistor R1 to pass a predetermined discrete pattern of electrical signals constituting a sonic profile, signature or imprint of the movement of a selected body part. For example, the up and down sidewise movement (abduction-abduction) of the human arms shown in FIG. 1 is movement of the humerus bone or upper arm bone in the shoulder, movement of the fibial relative to the femur e.g., the knee joint, provides subsonic sounds (apart from the audible snapping of joints) which are unique and distinctive.

Figure 4:
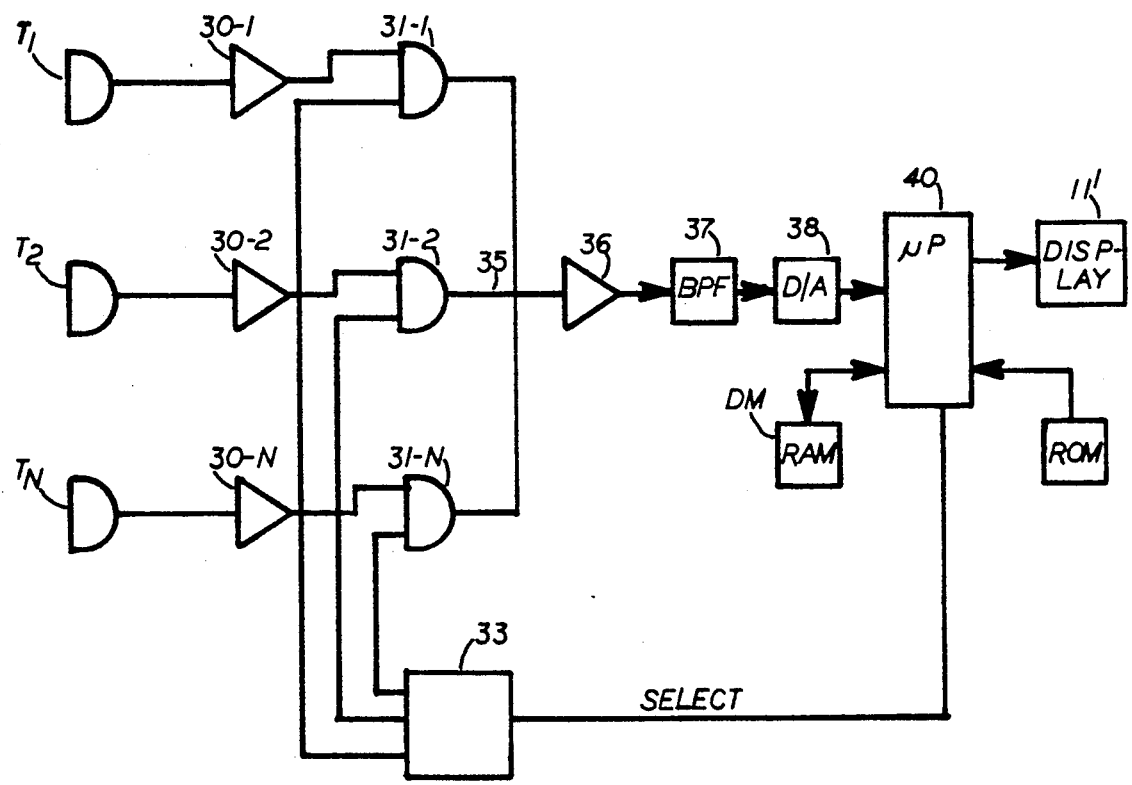

Referring now to the embodiment shown in FIG. 4, a plurality of transducers T1, T2 ... TN are amplified in preamplifiers 30-1, 30-2 ... 30-N. While the multiplexing operation can be performed either at the transducer head or in an electronic's compartment, in this embodiment, the multiplexing operation is performed at the transducer head. In this case, the gates 31-1, 31-2 ... 31-N receive gate signals from counter 33 via line "select". The gated analog signals are coupled by a coaxial cable 25 to an amplifier 36, bandpass filter 37BPF and analog-to-digital converter 38. The digital signals constituting the multiplexed output for the individual transducers are then supplied to the microprocessor 40 which controls the "select" line and, in turn, the counter 33.

In this case, the microprocessor 40 performs the filter and discriminator functions discussed earlier, identify and classify the acoustic signatures from the different body systems, and also operates the display 71 which may be a CRT, LCD, plasma, display.

In addition, a read-only memory ROM is provided for storing sonic profiles of large number of joints or cardiovascular flow in particular parts of the body which is used to compare with the incoming acoustic or sonic profiles so as to identify the sounds and the cardiovascular or skeletal from which they emanate. At the same time, microprocessor 40 stores for short term use data in a random access memory DM.

The entire spectrum of sonic signals for each joint in the skeletal system or the cardiovascular system and each part of the body may be detected, digitized and stored in a computer memory. For this purpose, a digital-to-analog converter DA is provided for converting each acoustic signature to a digital signal and processed by microprocessor MP and stored in a digital memory DM. Moreover, each acoustic signature may be analyzed and compared with a standard acoustic signature which has been derived from analysis of a large number of acoustic signatures. For example, a large number of individuals may be placed in vessel 10, and asked to move a particular part of their body in a particular fashion. For example, the human H shown in FIG. 1 is asked to point his right arm directly outwardly from the side and then move it in an arc up and down (while the shoulder joint is, of course, below the surface of the acoustically transmissive liquid ATL). See FIG. 2 for a sample of the various movements. A large number of individuals are asked to do the same articulation of their right arm. The acoustically recorded signatures for each individual are then analyzed to establish a norm or "standard" which may be stored in a read only memory ROM, along with other fixed program files. The standard may be according to age, sex, physical size (e.g., skeletal size). As another example, a group of individuals may each be asked individually to insert their leg into the acoustic transmissive liquid ATL and hold it stationary and the transducer 11 used to detect the infra subsonic signals made by the coursing of the blood flow through the cardiovascular system and thereby derive an acoustic signature to establish as a standard comparison. In like manner, individuals having a particular ailment may be asked to immerse a part of their body into the acoustically transmissive liquid and those known ailments then utilized as a base for establishing a characteristic departure from the standard. Numerous other examples of similar character may be given but it is believed that the above is sufficient to establish the broad implication and applications of the invention.

Since the acoustic signatures for different skeletal areas and parts of the human and flows in different parts of the cardiovascular system have their own characteristic acoustic signatures, transducers may constituted by a plurality of hydrophones T1, T2 ... TN for example, and bandpass filters, one utilized for example, for selected cardiovascular signals and one used for selected skeletal signals. Large numbers of individual channels may be utilized, each attuned to a particular skeletal sound or a particular cardiovascular sound. Finally, different combinations of skeletal and cardiovascular sounds may be utilized to detect and identify a particular individual or to detect and identify particular ailments and/or symptoms of ailments.

While there has been shown and described a preferred embodiments of the invention, it will be appreciated that various other adaptations and modifications of the invention will be readily apparent to those skilled in the art and it is intended to encompass such obvious modifications and adaptations in the spirit and scope of the claims appended hereto.

What is claimed is:

1. A non-invasive method of diagnosing ailments cardiovascular and skeletal system of a body comprising:
   (1) immersing the body in an acoustically transmissive liquid,
   (2) immersing a sonic transducer in the body of liquid and detecting sonic energy emitted by said body,
   (3) determining whether the acoustic energy is derived from the skeletal system of the body or from the cardiovascular system of the body,
   (4) storing said acoustic signatures in a storage medium and
   (5) analyzing said acoustic signatures to diagnose particular ailments of said body .

2. The invention defined in claim 1 wherein a predetermined number of said bodies are immersed in said liquid medium and acoustic signatures derived therefrom, and forming a library of acoustic signatures.

3. A non-invasive diagnostic apparatus comprising:
a vessel holding an acoustically transmissive liquid (ATL), said vessel being of sufficient size to hold at least a portion of the body of an animal therein such that said portion generate an acoustic signature and launch same into said acoustically transmissive liquid, said vessel having wall surfaces and means on said wall surfaces for preventing acoustic reflections therefrom, transducer means immersed in said body of acoustically transmissive liquid for converting acoustic energy travelling in said acoustically transmissive body of liquid to electrical signals, bandpass filter means connected to receive said electrical signals, means connected to said filter means for detecting the acoustic signatures of parts of said body as same is articulated therein.

4. The invention defined in claim 3 including means for identifying the portion of the body from which said acoustic signature originates.

5. The invention defined in claim 3 including means for storing a standard acoustic signature for a selected skeletal and cardiovascular part, and comparing subsequent acoustic signatures with said selected standard acoustic signature.

6. The invention defined in claims 1, 2 or 5 wherein said sonic energy is in the infrasonic range.

7. The invention defined in claim 3, 4 or 5 wherein said bandpass filter passes electrical signals in the infrasonic range.

* * * * *